United States Patent
Yakubo et al.

(10) Patent No.: US 10,717,658 B2
(45) Date of Patent: Jul. 21, 2020

(54) TITANIUM OXIDE PARTICLES, AND TITANIUM OXIDE PARTICLE DISPERSION AND COSMETICS USING SAME

(71) Applicant: SUMITOMO OSAKA CEMENT CO., LTD., Tokyo (JP)

(72) Inventors: Teppei Yakubo, Tokyo (JP); Tetsuro Itagaki, Tokyo (JP)

(73) Assignee: SUMITOMO OSAKA CEMENT CO., LTD., Tokyo (JP)

(*) Notice: Subject to any disclaimer, the term of this patent is extended or adjusted under 35 U.S.C. 154(b) by 0 days.

(21) Appl. No.: 16/313,426

(22) PCT Filed: Jun. 28, 2017

(86) PCT No.: PCT/JP2017/023745
§ 371 (c)(1),
(2) Date: Dec. 26, 2018

(87) PCT Pub. No.: WO2018/003851
PCT Pub. Date: Jan. 4, 2018

(65) Prior Publication Data
US 2019/0161360 A1  May 30, 2019

(30) Foreign Application Priority Data

Jun. 29, 2016 (JP) ................. 2016-129266

(51) Int. Cl.
| | | |
|---|---|---|
| *C01G 23/053* | (2006.01) | |
| *A61K 8/29* | (2006.01) | |
| *A61Q 1/12* | (2006.01) | |
| *A61K 8/04* | (2006.01) | |

(52) U.S. Cl.
CPC .............. *C01G 23/053* (2013.01); *A61K 8/04* (2013.01); *A61K 8/29* (2013.01); *A61Q 1/12* (2013.01); *A61K 2800/10* (2013.01); *A61K 2800/43* (2013.01); *C01P 2004/03* (2013.01); *C01P 2004/04* (2013.01); *C01P 2004/41* (2013.01); *C01P 2006/12* (2013.01); *C01P 2006/22* (2013.01)

(58) Field of Classification Search
CPC ........ A61K 8/29; A61K 8/04; A61K 2800/10; A61K 2800/43; A61Q 1/12; C01P 2004/03; C01P 2004/04; C01P 2004/41; C01P 2006/12; C01P 2006/22
See application file for complete search history.

(56) References Cited

U.S. PATENT DOCUMENTS 5,759,948 A  6/1998 Takaoka et al.

FOREIGN PATENT DOCUMENTS

| CN | 101152131 | * | 1/2013 |
|---|---|---|---|
| CN | 102849793 | * | 1/2013 |
| CN | 102849793 A | | 1/2013 |
| JP | 07-303835 A | | 11/1995 |
| JP | 10-139434 A | | 5/1998 |
| JP | 2000-239020 A | | 9/2000 |
| JP | 2001-029795 A | | 2/2001 |
| JP | 2007-106646 A | | 4/2007 |
| JP | 2009184972 | * | 8/2009 |

OTHER PUBLICATIONS

International Search Report for PCT/JP2017/023745 (dated Aug. 8, 2017).
Search Report for European Paten Application No. 17820205.7 (dated Nov. 7, 2019).

* cited by examiner

*Primary Examiner* — Shirley V Gembeh
(74) *Attorney, Agent, or Firm* — Merchant & Gould P.C.

(57) ABSTRACT

Titanium oxide particles of the present invention include octahedral-shaped particles, in which each particle of the octahedral-shaped particles has line segments each of which connects two apexes which face each other and has a maximum value of the line segments, an average value of the maximum values is 300 nm or more and 1,000 nm or less, and a value (the average value of the maximum values/BET-converted average particle diameter) obtained by dividing the average value of the maximum values of the line segments by an average particle diameter converted from a BET specific surface area is 1.0 or more and 2.5 or less.

8 Claims, 4 Drawing Sheets

TITANIUM OXIDE PARTICLES, AND TITANIUM OXIDE PARTICLE DISPERSION AND COSMETICS USING SAME

TECHNICAL FIELD

The present invention relates to titanium oxide particles suitable for cosmetics, and a titanium oxide particle dispersion and cosmetics using the same.

This application is a U.S. National Stage Application under 35 U.S.C. § 371 of International Patent Application No. PCT/JP2017/023745, filed on Jun. 28, 2017, which claims the benefit of priority to Japanese Patent Application No. 2016-129266, filed on Jun. 29, 2016, the disclosures of all of which are hereby incorporated by reference in their entireties. The International Application was published in Japanese on Jan. 4, 2018 as WO 2018/003851.

BACKGROUND

In the related art, base makeup cosmetics such as foundation are widely used in order to regulate the skin to a desired color, and to conceal pores or the like, so that the skin looks smooth. Generally, the base makeup cosmetics contain a pigment in order to regulate a color of the skin. As the pigment, titanium oxide is frequently used. As the titanium oxide, spherical-shaped and quadrangular-shaped titanium oxide particles have been used so far. However, in a case where base makeup cosmetics with which spherical-shaped or quadrangular-shaped titanium oxide particles are blended are used, there is a problem of resulting in a white floating phenomenon which makes the skin look whitish or causing deteriorated transparency which makes the skin look dull.

In order to solve this problem, for example, it has been proposed to use spindle-shaped titanium oxide particles, which are known for cosmetics, in base makeup cosmetics (see, for example, Patent Literature No. 1). However, in a case of being applied to the skin, the base makeup cosmetics with which the spindle-shaped titanium oxide particles are blended have a problem that paleness peculiar to titanium oxide appears.

For such reasons, there is a requirement for improvement of a feeling in use of the base makeup cosmetics with which the titanium oxide particles are blended. Specifically, there is a requirement for titanium oxide particles capable of decreasing paleness peculiar to titanium oxide particles while having a concealing ability and a feeling of transparency in a case of being applied to the skin.

CITATION LIST

Patent Literature

[Patent Literature No. 1] Japanese Laid-open Patent Publication No. 10-139434

SUMMARY OF INVENTION

Technical Problem

The present invention has been made in view of the above circumstances, and an object of the present invention is to provide titanium oxide particles capable of decreasing paleness peculiar to titanium oxide particles while having a concealing ability and a feeling of transparency in a case of being applied to the skin, and a titanium oxide particle dispersion and cosmetics using the same.

Solution to Problem

According to the first aspect of the present invention, there are provided titanium oxide particles that include octahedral-shaped particles, in which each particle of the octahedral-shaped particles has line segments each of which connects two apexes which face each other and has a maximum value of the line segments, an average value of the maximum values is 300 nm or more and 1,000 nm or less, and a value (the average value of the maximum values/BET-converted average particle diameter) obtained by dividing the average value of the maximum values of the line segments by an average particle diameter converted from a BET specific surface area is 1.0 or more and 2.5 or less.

The titanium oxide particles of the present invention preferably have the following features. These features may be combined with one another.

In the titanium oxide particles, an amount of the octahedral-shaped particles with respect to an entirety of the particles is preferably 50% by number or more.

In the titanium oxide particles, a specific surface area thereof is preferably 5 $m^2$/g or more and 15 $m^2$/g or less.

In a case where the maximum value is set as X (nm), and a minimum value of line segments, each of which is substantially orthogonal to a line segment which corresponds to the maximum value, and each of which connects two apexes which face each other in each particle of the octahedral-shaped particles, is set as Y (nm), an average value of ratios (X/Y) of the X to the Y is preferably 1.5 or more and 3.0 or less.

The titanium oxide particles preferably have an inorganic compound or an organic compound on a surface thereof.

According to the second aspect of the present invention, there is provided a titanium oxide particle dispersion which contains the titanium oxide particles and a dispersion medium.

According to the third aspect of the present invention, there are provided cosmetics which contain the titanium oxide particles and a cosmetic base.

Advantageous Effects of Invention

According to the titanium oxide particles of the present invention, it is possible to provide titanium oxide particles capable of decreasing paleness peculiar to titanium oxide particles while having a concealing ability and a feeling of transparency in a case of being applied to the skin, and a titanium oxide particle dispersion and cosmetics using the same.

According to the titanium oxide particle dispersion of the present invention, it is possible to decrease paleness peculiar to titanium oxide particles while having a concealing ability and a feeling of transparency in a case where cosmetics containing the titanium oxide particle dispersion is applied to the skin.

According to the cosmetics of the present invention, it is possible to decrease paleness peculiar to titanium oxide particles while having a concealing ability and a feeling of transparency in a case of being applied to the skin.

DESCRIPTION OF EMBODIMENTS

Embodiments of the titanium oxide particles of the present invention, and the titanium oxide particle dispersion and the cosmetics using the same will be described.

It is to be noted that the present embodiments will be described in detail in order to better understand the gist of the invention, and do not limit the present invention unless otherwise specified.

[Titanium Oxide Particles]

The titanium oxide particles of the present embodiment include octahedral-shaped particles, in which each particle of the octahedral-shaped particles has line segments each of which connects two apexes which face each other and has a maximum value of the line segments, an average value of the maximum values is 300 nm or more and 1,000 nm or less, and a value (the average value of the maximum values/BET-converted average particle diameter) obtained by dividing the average value of the maximum values of the line segments by an average particle diameter converted from a BET specific surface area is 1.0 or more and 2.5 or less.

Here, "each particle" means what is observed as one particle in a case of making an observation with an electron microscope. In a case where the particles do not agglomerate with one another, "each particle" means each primary particle. In a case where the primary particles agglomerate with one another to form agglomerated particles, "each particle" means each of the agglomerated particles, not each primary particle.

(Octahedral-Shaped Particles)

Figure 1:
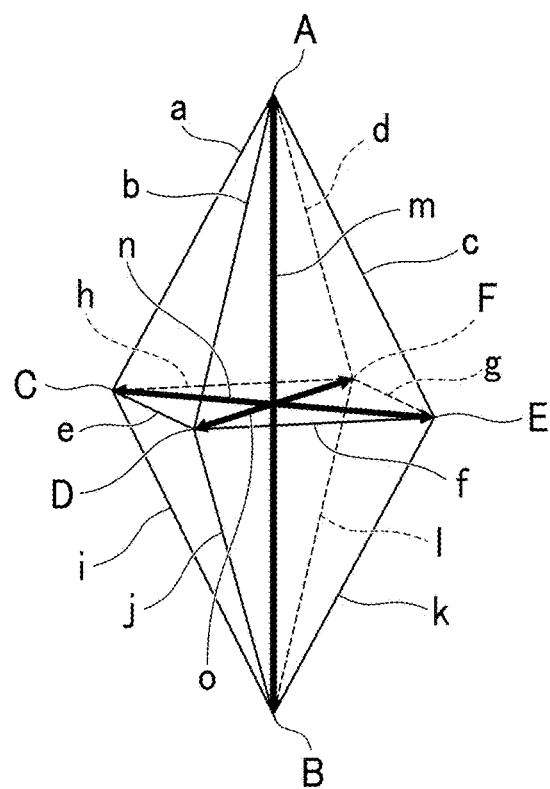
FIG. 1 is a schematic diagram showing an example of octahedral-shaped titanium oxide particles.

The titanium oxide particles of the present embodiment are aggregates of titanium oxide particles, and are octahedral-shaped titanium oxide particles (hereinafter referred to as "octahedral-shaped particles" in some cases). An octahedral shape is a three-dimensional shape in which space is surrounded by eight triangles, as shown in FIG. 1. A tip end part of the respective apexes of the octahedral-shaped titanium oxide particles (points indicated by reference signs A, B, C, D, E, and F in FIG. 1) may have a sharp shape, a rounded shape, or a flat shape.

In the titanium oxide particles of the present embodiment, an amount of the octahedral-shaped particles with respect to an entirety of the particles is preferably 50% by number or more, may be 60% by number or more, or may be 70% by number or more. In the titanium oxide particles of the present embodiment, an upper limit of the amount of the octahedral-shaped particles with respect to an entirety of the particles may be 80% by number or less, 90% by number or less, or 100% by number or less.

A case where the amount of the octahedral-shaped particles with respect to an entirety of the particles is 50% by number or more is advantageous from the viewpoint of further decreasing paleness peculiar to titanium oxide particles while having a concealing ability and a feeling of transparency in a case where cosmetics containing titanium oxide are applied to the skin.

The amount of the octahedral-shaped titanium oxide particles in the titanium oxide particles can be calculated, for example, by observing the titanium oxide particles with a scanning electron microscope, and counting the number of an entirety of the titanium oxide particles and the number of the octahedral-shaped titanium oxide particles included in the entirety of the titanium oxide particles.

(Line Segment which Connects Two Apexes which Face Each Other in Each Particle)

Each particle of the octahedral-shaped particles has line segments (hereinafter referred to as "distances between apexes" in some cases) each of which connects two apexes which face each other and has a maximum value of the line segments, and an average value of the maximum values in the octahedral-shaped particles is 300 nm or more and 1,000 nm or less, preferably 320 nm or more and 900 nm or less, more preferably 330 nm or more and 800 nm or less, and even more preferably 340 nm or more and 750 nm or less.

Octahedral-shaped particles, of which each particle has distances between two apexes which face each other and has a maximum value of the distances and in which an average value of the maximum values is 300 nm or more and 1,000 nm or less, are capable of scattering visible light over a wide range, as compared with spherical-shaped titanium oxide particles and spindle-shaped titanium oxide particles. Therefore, it is presumed that cosmetics which contain titanium oxide particles including the octahedral-shaped particles are capable of decreasing paleness peculiar to titanium oxide while achieving both a concealing ability and a feeling of transparency.

A case where each particle of the octahedral-shaped particles has distances between two apexes which face each other and has a maximum value of the distances, and an average value of the maximum values is 300 nm or more and 1,000 nm or less is advantageous from the viewpoint of further decreasing paleness peculiar to titanium oxide particles while having an excellent feeling of transparency in a case of being applied to the skin.

In a case where each particle of the octahedral-shaped particles has distances between two apexes which face each other and has a maximum value of the distances, and an average value of the maximum values is less than 300 nm, light having a short wavelength is scattered and a pale color is exhibited, which is not preferable. On the other hand, in a case where each particle of the octahedral-shaped particles has distances between two apexes which face each other and has a maximum value of the distances, and an average value of the maximum values is greater than 1,000 nm, a feeling of transparency is not obtained, which is not preferable.

A maximum value of distances between two apexes which face each other in each particle of the octahedral-shaped particles is measured by observing the octahedral-shaped particles with a scanning electron microscope (SEM). Specifically, with respect to one hundred particles of the octahedral-shaped particles, the maximum value of the distances between two apexes which face each other in each particle is measured, and the value obtained by arithmetically averaging the obtained measured values is an average value of the maximum values of the distances between two apexes which face each other.

In a case where a tip end part of the apexes of the octahedral-shaped titanium oxide particles is a flat surface, the maximum value of the distances between two apexes which face each other is measured by using a center point of the flat surface as the apex.

In a case where a maximum value of line segments (a long axis m of the octahedral-shaped particles in FIG. 1), each of which connects two apexes (points A and B in FIG. 1) which face each other in each particle of the octahedral-shaped particles is set as X (nm), and a minimum value of line segments (a short axis n or o of the octahedral-shaped particles in FIG. 1), each of which is substantially orthogonal to a line segment (a long axis m of the octahedral-shaped particles in FIG. 1) which corresponds to the maximum value, and each of which connects two apexes (points C and E, or points D and F in FIG. 1) which face each other in each particle of the octahedral-shaped particles, is set as Y (nm), an average value of ratios (X/Y) of the X to the Y is preferably 1.5 or more and 3.0 or less, and more preferably 1.5 or more and 2.5 or less.

A case where the average value of ratios (X/Y) is 1.5 or more and 3.0 or less is advantageous from the viewpoint that cosmetics which contain titanium oxide particles including the octahedral-shaped particles are capable of obtaining a light scattering effect of the octahedral-shaped particles in a more effective manner and of further improving a feeling of transparency in a case of being applied to the skin.

Being substantially orthogonal as described above indicates that two line segments (a long axis and a short axis of the octahedral-shaped particles) intersect at an angle of 70° to 90°. In addition, regarding being substantially orthogonal as described above, two line segments (the long axis and the short axis of the octahedral-shaped particles) may be close to each other and intersect each other, or two line segments (the long axis and the short axis of the octahedral-shaped particles) may not necessarily have an intersection point.

An octahedral shape is a shape in which two rectangular pyramids share a rectangular bottom surface. The maximum value (X) of distances between two apexes which face each other in each particle of the octahedral-shaped particles means a length of a line segment that gives a distance between two apexes present in a direction orthogonal with respect to the bottom surface of the rectangular pyramids. In addition, the minimum value (Y) of distances between two apexes which face each other in each particle of the octahedral-shaped particles means a length of a shorter diagonal line in two diagonal lines on the bottom surface of the two rectangular pyramids.

Here, the distance between two apexes will be described with reference to the drawings. FIG. 1 is a schematic diagram showing an example of octahedral-shaped titanium oxide particles in the titanium oxide particles of the present embodiment. In FIG. 1, as distances between two apexes in each particle of the octahedral-shaped particles, there are 15 distances of a distance a between points A and C, a distance b between points A and D, a distance c between points A and E, a distance d between points A and F, a distance e between points C and D, a distance f between the points D and E, a distance g between points E and F, a distance h between points F and C, a distance i between points B and C, a distance j between points B and D, a distance k between points B and E, a distance 1 between points B and F, a distance n between points C and E, a distance o between points D and F, and a distance m between points A and B. In FIG. 1, as distances between two apexes which face each other in each particle of the octahedral-shaped particles, there are 3 distances of the distance n between points C and E, the distance o between points D and F, and the distance m between points A and B. A maximum value of the distances between two apexes which face each other in each particle of the octahedral-shaped particles is the distance m, which corresponds to the maximum value (X) of the distances between two apexes which face each other in each particle of the octahedral-shaped particles. In addition, in FIG. 1, line segments each of which is substantially orthogonal to a line segment which corresponds to the maximum value X, and each of which connects two apexes which face each other in each particle of the octahedral-shaped particles are the distance n and the distance o. In the distance n and the distance o, a shorter distance corresponds to the minimum value (Y) of the distances between two apexes which face each other in each particle of the octahedral-shaped particles.

The maximum value (X) (nm) of the distances between two apexes which face each other in each particle of the octahedral-shaped particles, and the minimum value (Y) (nm) of the distances between two apexes which face each other in each particle of the octahedral-shaped particles can be measured, for example, by observing the octahedral-shaped particles using a scanning electron microscope (SEM).

The above ratio (X/Y) is calculated by observing the titanium oxide particles with a scanning electron microscope (SEM) and measuring the maximum value (X) and the minimum value (Y). For the 100 octahedral-shaped titanium oxide particles, the value obtained by calculating the respective ratios (X/Y) and arithmetically averaging the same is an average value of the above ratios (X/Y).

(Specific Surface Area)

A specific surface area of the titanium oxide particles of the present embodiment is preferably 5 $m^2/g$ or more and 15 $m^2/g$ or less, and more preferably 5 $m^2/g$ or more and 13 $m^2/g$ or less.

A case where the specific surface area of the titanium oxide particles is 5 $m^2/g$ or more and 15 $m^2/g$ or less is advantageous from the viewpoint of further decreasing paleness peculiar to titanium oxide.

As a method of measuring the specific surface area, for example, a method of performing measurement from a nitrogen adsorption isotherm by the BET multipoint method using a fully automated specific surface area measuring device (trade name: BELSORP-Mini II, manufactured by MicrotracBEL Corp.) is mentioned.

(Average Particle Diameter Converted from BET Specific Surface Area)

An average particle diameter of the titanium oxide particles which is converted from a BET specific surface area of the titanium oxide particles (hereinafter also referred to as "BET-converted average particle diameter") is preferably 300 nm or more and 1,000 nm or less, more preferably 310 nm or 800 nm or less, and even more preferably 320 nm or more and 700 nm or less.

The BET-converted average particle diameter of the titanium oxide particles can be calculated by Expression (1) since the titanium oxide particles have an octahedral shape.

BET-converted average particle diameter
 (nm)=16240/(BET specific surface area $(m^2/g)\times$
 $\rho(g/cm^3))$ (1)

In Expression (1), ρ represents a density of the titanium oxide particles.

In general, in a case where the octahedral-shaped particles do not agglomerate with one another, the average particle diameter of the octahedral-shaped particles which is converted from the BET specific surface area is roughly matches an arithmetic average value of maximum values, the maximum value being a maximum value of line segments each of which connects two apexes which face each other in each particle of the octahedral-shaped particles, and the maximum values are measured by making an observation with an electron microscope. In a case where primary particles agglomerate with one another to form the octahedral-shaped particles, an arithmetic average value of maximum values which are measured by making an observation with an electron microscope and in which the maximum value is a maximum value of line segments each of which connects two apexes which face each other in each particle (each of agglomerated particles) of the octahedral-shaped particles, does not match the average particle diameter of the octahedral-shaped particles which is converted from the BET specific surface area.

(Average Value of Maximum Values/BET-Converted Average Particle Diameter)

A value (average value of maximum values/BET-converted average particle diameter) obtained by dividing the average value of the maximum values by the average particle diameter of the octahedral-shaped particles which is converted from the BET specific surface area is 1.0 or more and 2.5 or less, preferably 1.0 or more and 1.4 or less, and more preferably 1.0 or more and 1.3 or less.

In a case where (the average value of the maximum values/the BET-converted average particle diameter) is less than 1.0, it is assumed that fine pores and the like are present in the titanium oxide particles, a refractive index as particles is lower than an original value of titanium oxide, which may, as a result, decrease a concealing ability. On the other hand, in a case where (the average value of the maximum values/the BET-converted average particle diameter) is greater than 2.5, in a case of applying cosmetics which contain the titanium oxide particles to the skin, it is not possible to obtain a light scattering effect due to a shape of the titanium oxide particles and thus it is not possible to improve a feeling of transparency.

In a case where the octahedral-shaped particles do not agglomerate with one another, the average particle diameter of the octahedral-shaped particles which is converted from the BET specific surface area is roughly matches an arithmetic average value of maximum values, the maximum value being a maximum value of line segments each of which connects two apexes which face each other in each particle of the octahedral-shaped particles, and the maximum values are measured by making an observation with an electron microscope. Therefore, the fact that the value of (the average value of the maximum values/the BET-converted average particle diameter) is closer to 1.0 means that the titanium oxide particles are less likely to agglomerate with one another and more particles are present in a state of primary particles.

(Crystalline Phase)

A crystalline phase of the titanium oxide particles of the present embodiment is not particularly limited, and may be any one single phase of an anatase type, a rutile type, and a brookite type, or may be a mixed phase thereof. Among these, the crystalline phase of the titanium oxide particles of the present embodiment is preferably the anatase type. A case where the crystalline phase of the titanium oxide particles is the anatase type is advantageous from the viewpoint that a concealing ability is further increased in a case where cosmetics containing the titanium oxide particles is applied to the skin, and a color which is close to a color of the human skin is obtained in a case of being mixed with a cosmetic base.

The fact that the titanium oxide particles have the anatase type can be confirmed by, for example, an X-ray diffractometer (trade name: X'Pert PRO, manufactured by Spectris Co., Ltd.). In a case where a measurement result by the X-ray diffractometer is an anatase single phase, titanium oxide particles have the anatase type.

(Surface Treatment)

The titanium oxide particles of the present embodiment may have an inorganic compound or an organic compound on a surface thereof.

As a method of attaching the inorganic compound or the organic compound to the surface of the titanium oxide particles, for example, a method of performing a surface treatment using a surface treatment agent, and the like are mentioned.

The surface treatment agent is not particularly limited as long as the surface treatment agent can be used in cosmetics, and can be appropriately selected depending on a purpose. As the surface treatment agent, an inorganic component and an organic component are mentioned.

As the inorganic component, silica, alumina, and the like are mentioned.

As the organic component, for example, a silicone compound, an organopolysiloxane, a fatty acid, fatty acid soap, fatty acid ester, an organic titanate compound, a surfactant, a non-silicone compound, and the like are mentioned. One of these may be used alone, or two or more thereof may be used in combination.

As the silicone compound, for example, silicone oil such as methyl hydrogen polysiloxane, dimethyl polysiloxane, and methylphenyl polysiloxane; alkyl silane such as methyl trimethoxysilane, ethyl trimethoxysilane, hexyl trimethoxysilane, and octyl trimethoxysilane; fluoroalkyl silane such as trifluoromethylethyl trimethoxysilane and heptadecafluorodecyl trimethoxysilane; methicone, hydrogen dimethicone, triethoxysilyl ethyl polydimethylsiloxyethyl dimethicone, triethoxysilylethylpolydimethylsiloxyethylhexyl dimethicone, (acrylates/acrylic acid tridecyl/triethoxysilylpropyl methacrylate/dimethicone methacrylate) copolymer, triethoxycaprylyl silane, and the like are mentioned. In addition, the silicone compound may be a monomer of a compound or a copolymer thereof. One of these may be used alone, or two or more thereof may be used in combination.

As the fatty acid, for example, palmitic acid, isostearic acid, stearic acid, lauric acid, myristic acid, behenic acid, oleic acid, rosin acid, 12-hydroxystearic acid, and the like are mentioned.

As the fatty acid soap, for example, aluminum stearate, calcium stearate, aluminum 12-hydroxystearate, and the like are mentioned.

As the fatty acid ester, for example, dextrin fatty acid ester, cholesterol fatty acid ester, sucrose fatty acid ester, starch fatty acid ester, and the like are mentioned.

As the organic titanate compound, for example, isopropyl triisostearoyl titanate, isopropyl dimethacryl isostearoyl titanate, isopropyl tri(dodecyl) benzene sulfonyl titanate, neopentyl (diallyl)oxy-tri(dioctyl) phosphate titanate, neopentyl (diallyl)oxy-trineododecanoyl titanate, and the like are mentioned.

According to the titanium oxide particles of the present embodiment, in a case where cosmetics containing the titanium oxide particles are applied to the skin, it is possible to obtain natural finish in which paleness peculiar to titanium oxide is decreased while achieving both a concealing ability and a feeling of transparency. Therefore, the titanium oxide particles of the present embodiment can be suitably used for cosmetics, and, in particular, can be suitably used for base makeup cosmetics.

[Method for Manufacturing Titanium Oxide Particles]

A method for manufacturing titanium oxide particles of the present invention has a first step of preparing a reaction solution by mixing a hydrolyzed product of a titanium alkoxide or a titanium metal salt with a compound having a five-membered ring that contains nitrogen, and subjecting this reaction solution to hydrothermal synthesis, to produce titanium oxide particles. In addition, the method for manufacturing titanium oxide particles of the present invention has, as necessary, a second step of mixing a reaction solution containing the titanium oxide particles which have been subjected to hydrothermal synthesis and are obtained in the first step with the same reaction solution as in the first step which have not been subjected to hydrothermal synthesis, and subjecting the mixture to hydrothermal synthesis.

(First Step)

The first step is a step of producing titanium oxide particles.

In the first step, the hydrolyzed product of titanium alkoxide or titanium metal salt is mixed with the compound having a five-membered ring that contains nitrogen to prepare a reaction solution, and this reaction solution is subjected to hydrothermal synthesis to produce titanium oxide particles.

(Hydrolyzed Product of Titanium Alkoxide or Titanium Metal Salt)

The hydrolyzed product of titanium alkoxide or titanium metal salt is obtained by hydrolyzing the titanium alkoxide or the titanium metal salt. The hydrolyzed product is, for example, a cake-like solid which is a white solid, and is hydrated titanium oxide called metatitanic acid or orthotitanic acid.

As the titanium alkoxide, for example, tetraethoxytitanium, tetraisopropoxytitanium, tetra-n-propoxytitanium, tetra-n-butoxytitanium, and the like are mentioned. One of these may be used alone, or two or more thereof may be used in combination. Among these, tetraisopropoxytitanium and tetra-n-butoxytitanium are preferable, and tetraisopropoxytitanium is more preferable, from the viewpoint of easy availability and easy control of a hydrolysis rate.

As the titanium metal salt, for example, titanium tetrachloride, titanium sulfate, and the like are mentioned. One of these may be used alone, or two or more thereof may be used in combination.

In the present embodiment, in order to obtain high-purity anatase type titanium oxide particles, it is preferable to use a high purity titanium alkoxide or a high purity titanium metal salt.

The hydrolyzed product contains a by-product such as alcohols, hydrochloric acid, and sulfuric acid.

Since the by-product inhibits nucleation and crystal growth of titanium oxide particles, it is preferable to clean the hydrolyzed product with pure water. As a method for cleaning the hydrolyzed product, for example, decantation, Nutsche method, ultrafiltration method, and the like are mentioned.

(Compound Having Five-Membered Ring that Contains Nitrogen)

The compound having a five-membered ring that contains nitrogen is contained in the reaction solution due to a function as a pH adjuster of the reaction solution and a function as a catalyst for hydrothermal synthesis.

As the compound having a five-membered ring that contains nitrogen, for example, pyrrole, imidazole, indole, purine, pyrrolidine, pyrazole, triazole, tetrazole, isothiazole, isoxazole, furazan, carbazole, 1,5-diazabicyclo-[4.3.0]-5-nonene, and the like are mentioned. One of these may be used alone, or two or more thereof may be used in combination.

Among these, as the compound having a five-membered ring that contains nitrogen, a compound containing one nitrogen atom is preferable from the viewpoint of narrowing a particle size distribution of titanium oxide particles and of further improving crystallinity, and, for example, pyrrole, indole, pyrrolidine, isothiazole, isoxazole, furazan, carbazole, and 1,5-diazabicyclo-[4.3.0]-5-nonene are preferable.

Among these, as the compound having a five-membered ring that contains nitrogen, a compound which contains one nitrogen atom and of which a five-membered ring has a saturated heterocyclic structure is preferable from the viewpoint of narrowing a particle size distribution of titanium oxide particles and of further improving crystallinity, and, for example, pyrrolidine, and 1,5-diazabicyclo-[4.3.0]-5-nonene are more preferable.

A method for preparing the reaction solution is not particularly limited, and can be appropriately selected depending on a purpose. For example, a method of mixing by using a stirrer, a bead mill, a ball mill, an attritor, a dissolver, or the like, and the like are mentioned.

In addition, water may be added to the reaction solution so that a concentration of the reaction solution is adjusted. As the water to be added to the reaction solution, deionized water, distilled water, pure water, and the like are mentioned.

A pH of the reaction solution is preferably 9 or more and 13 or less, and more preferably 11 or more and 13 or less, from the viewpoint that a catalytic action of the compound having a five-membered ring that contains nitrogen appropriately functions and a nucleation rate becomes appropriate.

In a case where the pH of the reaction solution is in a range of 9 or more and 13 or less, production of titanium oxide particles and efficiency of crystal growth become better.

The pH of the reaction solution can be regulated by controlling a content of the compound having a five-membered ring that contains nitrogen.

A titanium atom concentration in the reaction solution can be appropriately selected depending on a size of target titanium oxide particles, and the titanium atom concentration is preferably 0.05 mol/L or more and 3.0 mol/L or less, and more preferably 0.5 mol/L or more and 2.5 mol/L or less.

In a case where the titanium atom concentration in the reaction solution is 0.05 mol/L or more and 3.0 mol/L or less, a nucleation rate becomes appropriate, so that production of titanium oxide particles and efficiency of crystal growth become better.

The titanium atom concentration in the reaction solution can be regulated by controlling a content of the hydrolyzed product of titanium alkoxide or titanium metal salt.

A molar ratio (titanium atom:compound having a five-membered ring that contains nitrogen) of titanium atoms to compounds having a five-membered ring that contains nitrogen in the reaction solution is preferably 1.0:0.5 to 1.0:2.0, and more preferably 1.0:0.6 to 1.0:1.8, and even more preferably 1.0:0.7 to 1.0:1.5.

In a case where the molar ratio of titanium atoms to compounds having a five-membered ring that contains nitrogen in the reaction solution is within the above-mentioned range, it is possible to produce octahedral-shaped titanium oxide particles.

Hydrothermal synthesis is a method in which a reaction solution is heated to allow titanium in the reaction solution to react in the presence of high-temperature and high-pressure hot water.

The hydrothermal synthesis is carried out by placing a reaction solution in a high-temperature and high-pressure container called an autoclave, sealing the autoclave, and heating the reaction solution together with the autoclave.

In a case where the reaction solution is heated, a pressure in the container rises due to evaporation of moisture in the reaction solution, which allows a high-temperature and high-pressure reaction to occur.

A heating and holding temperature in the hydrothermal synthesis is preferably 150° C. or more and 350° C. or less, and more preferably 150° C. or more and 210° C. or less. In a case where the heating and holding temperature in hydrothermal synthesis is within the above-mentioned range, the hydrolyzed product of titanium alkoxide or titanium metal salt can have an improved solubility in water and can be dissolved in the reaction solution. In addition, the above case allows nuclei of titanium oxide particles to be produced and allows the nuclei to be grown, so that titanium oxide particles of a desired shape can be manufactured.

A heating rate in the hydrothermal synthesis is not particularly limited, and can be appropriately selected depending on a purpose.

A pressure in the hydrothermal synthesis is a pressure in a case where the reaction solution is heated to the above-mentioned temperature range in a high-temperature and high-pressure container.

During heating in the autoclave, it is preferable to stir the reaction solution using a stirring device.

A stirring speed is not particularly limited, and can be appropriately selected depending on a purpose. The stirring speed is preferably 100 rpm or more and 300 rpm or less.

A heating and holding time in the hydrothermal synthesis is not particularly limited, and can be appropriately selected depending on a size of the titanium oxide particles to be produced. The heating and holding time is preferably 3 hours or longer, and more preferably 4 hours or longer.

In a case where the heating and holding time is shorter than 3 hours, the hydrolyzed product of titanium alkoxide or titanium metal salt as a raw material may not react and a yield may decrease.

The heating and holding time is influenced by a type and a concentration of the raw material. Therefore, an appropriate preliminary experiment may be conducted, so that the hydrothermal synthesis is carried out for a heating and holding time which allows titanium oxide particles to have a desired size. For example, the heating and holding time may be 9 hours, 12 hours, 24 hours, 48 hours, or 72 hours. However, from the viewpoint of production efficiency, heating may be stopped at a time point where titanium oxide particles reach a desired size.

(Second Step)

The second step is a step of crystal-growing the titanium oxide particles obtained in the first step. The second step is carried out in a case where a size of the titanium oxide particles obtained is smaller than a desired size.

The second step is a step of mixing a reaction solution containing the titanium oxide particles which have been subjected to hydrothermal synthesis and are obtained in the first step with the same reaction solution (the hydrolyzed product of titanium alkoxide or titanium metal salt, and the compound having a five-membered ring that contains nitrogen) as in the first step which have not been subjected to hydrothermal synthesis, and subjecting the mixture to hydrothermal synthesis.

A mixing ratio of the reaction solution containing the titanium oxide particles which have been subjected to hydrothermal synthesis and are obtained in the first step to the same reaction solution (the hydrolyzed product of titanium alkoxide or titanium metal salt, and the compound having a five-membered ring that contains nitrogen) as in the first step which have not been subjected to hydrothermal synthesis is preferably 1:1 to 1:20 in a case of being converted by mass of titanium oxide particles.

A hydrothermal synthesis in the second step can be carried out under the same conditions as in the first step.

A method of taking out the titanium oxide particles from the mixed solution after carrying out the first step and the second step is not particularly limited, and can be appropriately selected depending on a purpose. As the method of taking out the titanium oxide particles from the mixed solution, for example, a method of performing solid-liquid separation such as decantation and Nutsche method, and the like are mentioned.

After taking out the titanium oxide particles, the obtained titanium oxide particles may be cleaned with pure water or the like for the purpose of decreasing impurities.

The titanium oxide particles taken out by solid-liquid separation may be dried by a known method.

It is also possible to subject the titanium oxide particles to a surface treatment. A timing of performing the surface treatment is not particularly limited, and can be appropriately selected depending on a purpose. As the timing of performing the surface treatment, for example, after the first step, after the second step, and the like are mentioned. A method of performing the surface treatment is not particularly limited, and a known method can be appropriately selected depending on a type of a surface treatment agent to be used.

[Titanium Oxide Particle Dispersion]

The titanium oxide particle dispersion of the present embodiment contains the titanium oxide particles of the present embodiment and a dispersion medium. The titanium oxide particle dispersion of the present embodiment contains other components as necessary.

The titanium oxide particle dispersion may be in a low-viscosity liquid state or a high-viscosity paste state.

A content of the titanium oxide particles in the titanium oxide particle dispersion is not particularly limited, and can be appropriately selected depending on a purpose.

(Dispersion Medium)

The dispersion medium is not particularly limited as long as the dispersion medium can be blended with cosmetics, and can be appropriately selected depending on a purpose. As the dispersion medium, for example, water, alcohols, esters, ethers, ketones, hydrocarbon, amides, polysiloxanes, modified polysiloxanes, hydrocarbon oil, ester oil, a higher fatty acid, higher alcohol, and the like are mentioned. One of these may be used alone, or two or more thereof may be used in combination.

As the alcohols, for example, methanol, ethanol, 1-propanol, 2-propanol, 1-butanol, 2-butanol, octanol, glycerin, and the like are mentioned.

As the esters, for example, ethyl acetate, butyl acetate, ethyl lactate, propylene glycol monomethyl ether acetate, propylene glycol monoethyl ether acetate, γ-butyrolactone, and the like are mentioned.

As the ethers, for example, diethyl ether, ethylene glycol monomethyl ether (methyl cellosolve), ethylene glycol monoethyl ether (ethyl cellosolve), ethylene glycol monobutyl ether (butyl cellosolve), diethylene glycol monomethyl ether, diethylene glycol monoethyl ether, and the like are mentioned.

As the ketones, for example, acetone, methyl ethyl ketone, methyl isobutyl ketone, acetyl acetone, cyclohexanone, and the like are mentioned.

As the hydrocarbon, for example, aromatic hydrocarbon such as benzene, toluene, xylene, and ethylbenzene; cyclic hydrocarbon such as cyclohexane, and the like are mentioned.

As the amides, dimethylformamide, N,N-dimethylacetoacetamide, N-methylpyrrolidone, and the like are mentioned.

As the polysiloxanes, for example, chain-like polysiloxanes such as dimethylpolysiloxane, methylphenylpolysiloxane, and diphenylpolysiloxane; cyclic polysiloxanes such as octamethylcyclotetrasiloxane, decamethylcyclopentasiloxane, and dodecamethylcyclohexasiloxane, and the like are mentioned.

As the modified polysiloxanes, for example, an amino-modified polysiloxane, a polyether-modified polysiloxane, an alkyl-modified polysiloxane, a fluorine-modified polysiloxane, and the like are mentioned.

As the hydrocarbon oil, for example, liquid paraffin, squalane, isoparaffin, branched chain-like light paraffin, petrolatum, ceresin, and the like are mentioned.

As the ester oil, for example, isopropyl myristate, cetyl isooctanoate, glyceryl trioctanoate, and the like are mentioned.

As the higher fatty acid, for example, lauric acid, myristic acid, palmitic acid, stearic acid, and the like are mentioned.

As the higher alcohol, for example, lauryl alcohol, cetyl alcohol, stearyl alcohol, hexyl dodecanol, isostearyl alcohol, and the like are mentioned.

(Other Components)

The other components are not particularly limited as long as the components do not impair an effect of the titanium oxide particle dispersion of the present embodiment, and can be appropriately selected depending on a purpose. As the other components, for example, a dispersant, a stabilizer, a water-soluble binder, a thickener, an oil-soluble preservative, an ultraviolet absorber, an oil-soluble agent, oil-soluble coloring matters, oil-soluble proteins, a vegetable oil, an animal oil, and the like are mentioned. One of these may be used alone, or two or more thereof may be used in combination.

A content of the dispersion medium is not particularly limited, and can be appropriately selected depending on a purpose. A content of the dispersion medium is preferably 10% by mass or more and 99% by mass or less, more preferably 20% by mass or more and 90% by mass or less, and even more preferably 30 mass % or more and 80 mass % or less, with respect to a total amount of the titanium oxide particle dispersion.

According to the titanium oxide particle dispersion of the present embodiment, in a case where cosmetics containing the titanium oxide particle dispersion is applied to the skin, it is possible to obtain natural finish in which paleness peculiar to titanium oxide is decreased while achieving both a concealing ability and a feeling of transparency. Therefore, the titanium oxide particle dispersion of the present embodiment can be suitably used for cosmetics, and, in particular, can be suitably used for base makeup cosmetics.

[Method for Manufacturing Titanium Oxide Particle Dispersion]

A method for manufacturing the titanium oxide particle dispersion of the present embodiment is not particularly limited, and a known method can be adopted. As the method for manufacturing the titanium oxide particle dispersion of the present embodiment, for example, a method of manufacturing a dispersion by mechanically dispersing the titanium oxide particles of the present embodiment with respect to a dispersion medium by a dispersing device, and the like are mentioned. As the dispersing device, a stirrer, a self-revolution type mixer, a homomixer, an ultrasonic homogenizer, a sand mill, a ball mill, a roll mill, and the like are mentioned.

In a case of being applied to the skin, the titanium oxide particle dispersion of the present embodiment is capable of decreasing paleness peculiar to titanium oxide while achieving both a concealing ability and a feeling of transparency.

[Cosmetics]

The cosmetics of the present embodiment contain the titanium oxide particles of the present embodiment and a cosmetic base. The cosmetics of the present embodiment contain other components as necessary.

A content of the titanium oxide particles in the cosmetics is preferably 0.1% by mass or more and 50% by mass or less, with respect to a total of the cosmetics.

(Cosmetic Base)

The cosmetic base can be appropriately selected from cosmetic bases usually used in cosmetics, and, for example, talc, mica, and the like are mentioned. One of these may be used alone, or two or more thereof may be used in combination.

A content of the cosmetic base in the cosmetics is not particularly limited, and can be appropriately selected depending on a purpose.

(Other Components)

In addition to the titanium oxide particles and the cosmetic base of the present embodiment, the cosmetics of the present embodiment can contain other components within a range which does not impair an effect of the present embodiment.

The other components can be appropriately selected from components usually used in cosmetics. As the other components, for example, a solvent, an oil agent, a surfactant, a humectant, an organic ultraviolet absorber, an antioxidant, a thickener, a fragrance, a colorant, a physiologically active component, an antibacterial agent, and the like are mentioned. One of these may be used alone, or two or more thereof may be used in combination.

A content of the other components in the cosmetics is not particularly limited, and can be appropriately selected depending on a purpose.

A method for manufacturing the cosmetics of the present embodiment is not particularly limited, and can be appropriately selected depending on a purpose. As the method for manufacturing the cosmetics of the present embodiment, for example, a manufacturing method in which the titanium oxide particles are mixed with the cosmetic base and the mixture is mixed with the other components, a manufacturing method in which the titanium oxide particles are mixed with existing cosmetics, a manufacturing method in which the titanium oxide particle dispersion is mixed with the cosmetic base and the mixture is mixed with the other components, and a manufacturing method in which the titanium oxide particle dispersion is mixed with existing cosmetics, and the like are mentioned.

(Form)

A form of the cosmetics of the present embodiment is not particularly limited, and can be appropriately selected depending on a purpose. As the form of the cosmetics of the present embodiment, for example, a powder-like form, powdery solid-like form, a solid-like form, a liquid-like form, a gel-like form, and the like are mentioned. In a case where the form of the cosmetics is liquid-like or gel-like, a dispersion form of the cosmetics is not particularly limited, and can be appropriately selected depending on a purpose. As the dispersion form of the gel-like cosmetics, for example, a water-in-oil type (W/O type) emulsion, an oil-in-water type (O/W type) emulsion, an oil type, and the like are mentioned.

As the cosmetics of the present embodiment, for example, base makeup, nail polish, lipstick, and the like are mentioned. Among these, the base makeup is preferable.

As the base makeup, for example, makeup base used mainly for decreasing irregularities of the skin, foundation used mainly for adjusting a color of the skin, face powder used mainly for improving fixation of foundation to the skin, and the like are mentioned.

According to the cosmetics of the present embodiment, it is possible to decrease paleness peculiar to titanium oxide particles while having a concealing ability and a feeling of transparency in a case of being applied to the skin.

EXAMPLES

Hereinafter, the present invention will be described more specifically with reference to Examples and Comparative Examples. However, the present invention is not limited to the following Examples.

Example 1

(Production of Titanium Oxide Particles)

1 L of pure water was placed in a glass container having a capacity of 2 L, and 1 mol of tetraisopropoxytitanium (trade name: A-1, manufactured by Nippon Soda Co., Ltd.) was added dropwise while performing stirring, to obtain a white suspension which is a hydrolyzed product of a titanium alkoxide.

Next, the white suspension was subjected to solid-liquid separation, to obtain a white cake which is a solid portion of the hydrolyzed product of titanium alkoxide.

Next, pyrrolidine (manufactured by Kanto Chemical Co., Inc.) in an amount of 0.7 mol with respect to 1 mol of titanium oxide in the white cake, and the white cake were placed in an autoclave, and pure water was added to make a total amount of 1 kg. The resultant was held at 220° C. for 9 hours to obtain a reaction solution containing titanium oxide particles.

The reaction solution containing titanium oxide particles was subjected to solid-liquid separation and the solid was dried at 200° C., to obtain titanium oxide particles of Example 1.

(Measurement of Specific Surface Area and Average Particle Diameter Converted from BET Specific Surface Area)

A specific surface area of the titanium oxide particles of Example 1 was measured using a specific surface area meter (trade name: BELSORP-mini, manufactured by Bel Japan, Inc.). As a result, the specific surface area of the titanium oxide particles of Example 1 was 13 m²/g.

An average particle diameter of the titanium oxide particles of Example 1 which is converted from a BET specific surface area was calculated by Expression (1). As a result, a BET-converted average particle diameter was 312 nm.

BET-converted average particle diameter (nm)=16240/(BET specific surface area (m²/g)× ρ(g/cm³)) (1)

In Expression (1), ρ represents a density of the titanium oxide particles, and ρ=4 g/cm³.

(Measurement of Shape)

"Measurement of Line Segment which Connects Two Apexes which Face Each Other"

Figure 2:
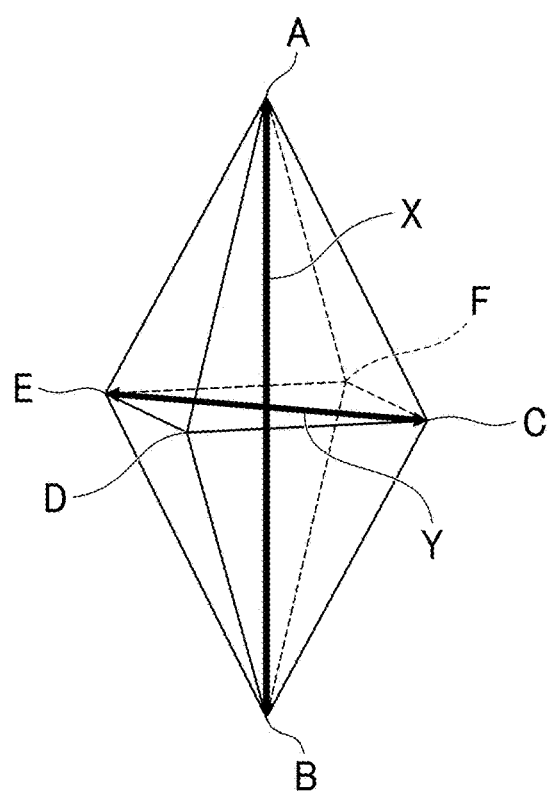
FIG. 2 is another schematic diagram showing an example of octahedral-shaped titanium oxide particles.

In FIG. 2, a maximum value (hereinafter indicated by (X)) of line segments each of which connects two apexes which face each other in each particle, and a minimum value (hereinafter indicated by (Y)) of line segments, each of which is substantially orthogonal to a line segment which corresponds to the maximum value, and each of which connects two apexes which face each other, were measured with a scanning electron microscope (SEM) (trade name: S-4800, manufactured by Hitachi High-Technologies Corporation) by observing a secondary electron image of the titanium oxide particles of Example 1.

100 titanium oxide particles of Example 1 were observed, and an average value of the above (X), an average value of the above (Y), and an average value of ratios (X/Y) of the X to the Y were calculated. As a result, the average value of the (X) was 350 nm, a value (hereinafter referred to as "average value of (X)/BET-converted average particle diameter" in some cases) obtained by dividing the average value of the (X) by the BET-converted average particle diameter was 1.1, and the average value of the ratios (X/Y) was 2.0.

Figure 3:
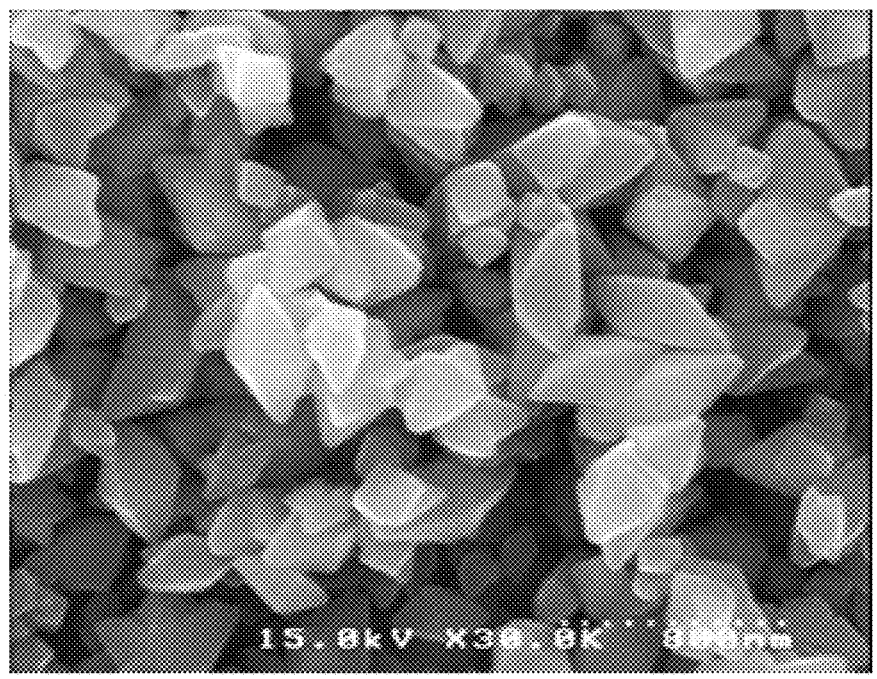
FIG. 3 is a view showing a scanning electron microscope image of an example of titanium oxide particles of Example 1.

In addition, octahedral-shaped titanium oxide particles were present in an amount of 70% by number with respect to an entirety of the particles. An SEM image of the titanium oxide particles of Example 1 is shown in FIG. 3.

"Identification of Shape of Titanium Oxide Particles"

Figure 4:
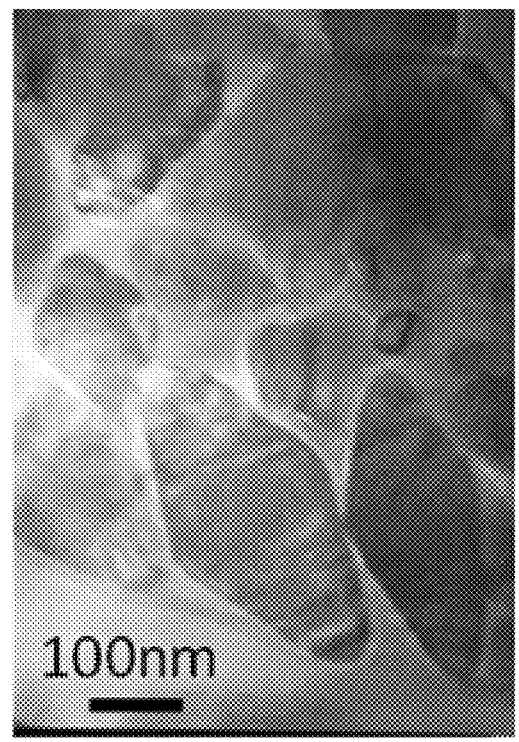
FIG. 4 is a view showing a transmission electron microscope image of an example of the titanium oxide particles of Example 1.

The titanium oxide particles of Example 1 were observed with a transmission electron microscope (TEM) (model number: H-800, manufactured by Hitachi High-Technologies Corporation). The results are shown in FIG. 4. Also in a TEM image, it was confirmed that the titanium oxide particles had an octahedral shape.

(Identification of Crystalline Phase of Titanium Oxide Particles)

A crystalline phase of the titanium oxide particles of Example 1 was identified using an X-ray diffractometer (trade name: X'PertPRO, manufactured by Spectris Co., Ltd.). As a result, the titanium oxide particles of Example 1 were in an anatase single phase.

Example 2

100 g (8 g of titanium oxide content) of a reaction solution containing the titanium oxide particles obtained in the production process of Example 1, the white cake (80 g of titanium oxide content) obtained in the production process of Example 1, and 0.7 mol of pyrrolidine were placed in an autoclave, and pure water was added to make a total amount to 1 kg. The resultant was stirred to produce a mixed solution.

Next, the mixed solution was held at 220° C. for 9 hours to crystal-grow the titanium oxide particles, so that a reaction solution containing the titanium oxide particles was obtained.

Next, the obtained reaction solution containing the titanium oxide particles was subjected to solid-liquid separation and dried at 200° C., to obtain titanium oxide particles of Example 2.

With regard to the obtained titanium oxide particles of Example 2, a specific surface area, a shape, and a crystalline phase were measured in the same manner as in Example 1.

As a result, the specific surface area was 9 m²/g, and a BET-converted average particle diameter was 451 nm. An average value of (X) was 450 nm, an average value of the (X)/the BET-converted average particle diameter was 1.0, and an average value of ratios (X/Y) was 2.0.

In addition, in the titanium oxide particles of Example 2, octahedral-shaped titanium oxide particles were 65% by number with respect to an entirety of the particles, and a crystalline phase of the titanium oxide particles was in an anatase single phase.

Example 3

100 g (8.8 g of titanium oxide content) of a reaction solution containing titanium oxide particles obtained in the production process of Example 2, the white cake (1 mol (80 g) of titanium oxide content) obtained in the production process of Example 1, and 0.7 mol of pyrrolidine were placed in an autoclave, and pure water was added to make a total amount to 1 kg. The resultant was stirred to produce a mixed solution.

Next, the mixed solution was held at 220° C. for 9 hours to obtain a reaction solution containing the titanium oxide particles.

Next, the obtained reaction solution containing the titanium oxide particles was subjected to solid-liquid separation and dried at 200° C., to obtain titanium oxide particles of Example 3.

With regard to the obtained titanium oxide particles of Example 3, a specific surface area, a shape, and a crystalline phase were measured in the same manner as in Example 1.

As a result, the specific surface area was 6 m²/g, and a BET-converted average particle diameter was 677 nm. An average value of (X) was 740 nm, the average value of the (X)/the BET-converted average particle diameter was 1.1, and an average value of ratios (X/Y) was 2.0.

In addition, in the titanium oxide particles of Example 3, octahedral-shaped titanium oxide particles were 60% by number with respect to an entirety of the particles, and a crystalline phase of the titanium oxide particles was in an anatase single phase.

Comparative Example 1

Commercially available titanium oxide particles having an average diameter of 300 nm and having a spherical-shaped rutile type with a specific surface area of 6 m²/g were used as titanium oxide particles of Comparative Example 1.

With respect to the titanium oxide particles of Comparative Example 1, measurement of a specific surface area was performed in the same manner as in Example 1, and as a result, the specific surface area was 6 m²/g. In addition, a BET-converted average particle diameter was calculated by Expression (2). As a result, the BET-converted average particle diameter was 250 nm, and a value obtained by dividing the average particle diameter by the BET-converted average particle diameter was 1.2.

$$\text{BET-converted average particle diameter (nm)}=6000/(\text{BET specific surface area (m}^2\text{/g)}\times\rho(\text{g/cm}^3)) \quad (2)$$

In Expression (2), $\rho$ represents a density of titanium oxide particles, and therefore, $\rho=4$ g/cm³. An average particle diameter of spherical-shaped particles which is converted from a BET specific surface area roughly matches an average diameter of primary particles.

In addition, in the titanium oxide particles of Comparative Example 1, an average value of (X) was 300 nm, the average value of the (X)/the BET-converted average particle diameter was 1.2, and an average value of ratios (X/Y) was 1.0. In the spherical-shaped titanium oxide particles, a diameter at a predetermined position corresponds to a maximum value (X) of line segments each of which connects two apexes which face each other in each particle. In the spherical-shaped titanium oxide particles, another diameter which is substantially orthogonal to the diameter at a predetermined position corresponds to a minimum value (Y) of line segments, each of which is substantially orthogonal to a line segment which corresponds to the maximum value (X), and each of which connects two apexes which face each other.

In addition, in the titanium oxide particles of Comparative Example 1, an amount of octahedral-shaped titanium oxide particles was 0% by number with respect to an entirety of the particles.

Comparative Example 2

Commercially available titanium oxide particles, of which primary particles area spheroid having an average major diameter of 100 nm and an average minor diameter of 30 nm and the primary particles agglomerate with one another to form a spindle shape with an average major diameter (average major diameter at agglomeration) of 300 nm, an average minor diameter (average minor diameter at aggregation) of 136 nm, and an average value of the major diameter at aggregation/the minor diameter at aggregation of 2.2, and which is a rutile type with a specific surface area of 21 m²/g, were used as titanium oxide particles of Comparative Example 2.

Since a shape of the primary particles is a spheroid, a BET-converted average particle diameter was calculated using Expression (3) with P=50 nm (100 nm÷2) and Q=3.33 (100÷30). As a result, the BET-converted average particle diameter was 100 nm.

$$\text{BET specific surface area (m}^2\text{/g)}=1000\times(1+P/((1-(1/Q)^2))^{1/2}\times P\times(1-(1/Q)^2)^{1/2}\times\sin^{-1}((1-(1/Q)^2)^{1/2}))/(2\times\rho\times P/3) \quad (3)$$

In Expression (3), $\rho$ represents a density of titanium oxide particles, and $\rho=4$ g/cm³.

In addition, in Expression (3), P represents a radius (nm) of the average major diameter of the spheroid which is the primary particles, and Q represents an average value of aspect ratios obtained by dividing a radius of a major axis (major diameter of primary particles/2) by a radius of a minor axis (minor diameter of primary particles/2).

In addition, in the titanium oxide particles of Comparative Example 2, an average value of (X) was 300 nm, the average value of the (X)/BET-converted average particle diameter was 3.0, and an average value of ratios (X/Y) was 2.2. Since the spindle-shaped titanium oxide particles of Comparative Example 2 agglomerate with one another, the average major diameter (average major diameter at agglomeration) corresponds to the maximum value (X) and the average minor diameter (average minor diameter at agglomeration) which is substantially orthogonal to a line segment which corresponds to the maximum value (X) corresponds to the minimum value (Y).

The value obtained by dividing the major diameter at agglomeration by the BET-converted average particle diameter was 3.0.

Since the titanium oxide particles of Comparative Example 2 aggregate with one another, a major diameter of an agglomerate and an average particle diameter converted from the BET specific surface area deviate from each other, and as a result, the major diameter of the agglomerate/the BET-converted average particle diameter greatly exceeds 1.5.

In addition, in the titanium oxide particles of Comparative Example 2, an amount of octahedral-shaped titanium oxide particles was 0% by number with respect to an entirety of the particles.

Comparative Example 3

Titanium oxide particles of Comparative Example 3 were obtained in the same manner as in Example 1 except that the resultant was held at 220° C. for 3 hours in place of being held at 220° C. for 9 hours in Example 1.

With regard to the obtained titanium oxide particles of Comparative Example 3, a specific surface area, a shape, and a crystalline phase were measured in the same manner as in Example 1.

As a result, the specific surface area was 22 m²/g, and a BET-converted average particle diameter was 185 nm. An average value of (X) was 220 nm, the average value of the (X)/the BET-converted average particle diameter is 1.2, and an average value of ratios (X/Y) was 2.0.

In addition, in the titanium oxide particles of Comparative Example 3, an amount of octahedral-shaped titanium oxide particles was 70% by number with respect to an entirety of the particles, and the crystalline phase of the titanium oxide particles was in an anatase single phase.

Comparative Example 4

Titanium oxide particles of Comparative Example 4 were obtained in the same manner as in Example 3 except that 100 g (8.8 g of titanium oxide content) of a reaction solution containing the titanium oxide particles obtained in the production process of Example 3 was used in place of 100 g (8.8 g of titanium oxide content) of a reaction solution containing the titanium oxide particles obtained in the production process of Example 2 in Example 3.

With regard to the obtained titanium oxide particles of Comparative Example 4, a specific surface area, a shape, and a crystalline phase were measured in the same manner as in Example 1.

As a result, the specific surface area was 4 m²/g, and a BET-converted average particle diameter was 1,015 nm. An average value of (X) was 1,200 nm, the average value of the (X)/the BET-converted average particle diameter is 1.2, and an average value of ratios (X/Y) was 2.0.

In addition, in the titanium oxide particles of Comparative Example 4, an amount of octahedral-shaped titanium oxide particles was 65% by number with respect to an entirety of the particles, and the crystalline phase of the titanium oxide particles was in an anatase single phase.

Comparative Example 5

Spherical-shaped rutile-type titanium oxide particles (commercial product) having an average diameter of 500 nm and a specific surface area of 4 m²/g were used as titanium oxide particles of Comparative Example 5.

With respect to the titanium oxide particles of Comparative Example 5, a BET-converted average particle diameter was calculated in the same manner as in Comparative Example 1, and as a result, the BET-converted average particle diameter was 375 nm. In addition, the value obtained by dividing the average diameter by the BET-converted average particle diameter is 1.3.

In addition, in the titanium oxide particles of Comparative Example 3, an average value of (X) is 500 nm, the average value of the (X)/the BET-converted average particle diameter was 1.3, and an average value of ratios (X/Y) was 1.0. In the spherical-shaped titanium oxide particles, a diameter at an optionally selected position corresponds to the maximum value (X) of line segments each of which connects two apexes which face each other in each particle. In the spherical-shaped titanium oxide particles, another diameter which is substantially orthogonal to the diameter at the optionally selected position corresponds to the minimum value (Y) of line segments, each of which is substantially orthogonal to a line segment which corresponds to the maximum value (X), and each of which connects two apexes which face each other.

In addition, in the titanium oxide particles of Comparative Example 5, an amount of octahedral-shaped titanium oxide particles was 0% by number with respect to an entirety of the particles.

(Evaluation of Cosmetics)
"Production of Cosmetics"

2 g of titanium oxide particles of each of Examples 1 to 3 and Comparative Examples 1 to 5, and 8 g of talc were mixed to prepare base makeup cosmetics of each of Examples 1 to 3 and Comparative Examples 1 to 5.

Each of the obtained base makeup cosmetics was applied on a 5 cm square substrate (trade name: HELIOPLATE HD-6, manufactured by Helioscreen) so as to be 12 mg to 14 mg, to produce applied substrates.

For each of the applied substrates, diffuse transmission spectrum (TT), diffuse reflection spectrum (TR), and linear reflection spectrum (R) were measured using a spectrophotometer (model number; UV-3150, manufactured by Shimadzu Corporation), and evaluation was performed using the following indices. In each case, an incident direction of light was measured from an applied surface, and the reflection spectrum was measured on the basis of a molded plate obtained by compressing barium sulfate powders (special grade, manufactured by Kanto Chemical Co., Inc.).

The results are shown in Table 1.

(Paleness)
A ratio ($TR_{450nm}/TR_{550nm}$) of a diffuse reflectance ($TR_{450nm}$) at 450 nm to a diffuse reflectance ($TR_{550nm}$) at 550 nm was used as an index for paleness. Since it can be said as being paler as the ratio becomes larger than 1, it is preferable that the value of $TR_{450nm}/TR_{550nm}$ is smaller.

A correlation between the index for paleness and an appearance viewed by human's eyes is shown in Table 2.

(Feeling of Transparency)
A ratio ($R_{550nm}/TR_{550nm}$) of a linear reflectance ($R_{550nm}$) at 550 nm and the diffuse reflectance ($TR_{550nm}$) at 550 nm was used as an index for feeling of transparency.

Since a smaller ratio indicates a higher feeling of transparency, it is preferable that the value is smaller.

A correlation between the index for feeling of transparency and an appearance viewed by human's eyes is shown in Table 2.

(Concealing Ability)
The diffuse reflectance ($TR_{550nm}$) at 550 nm was used as an index for concealing ability. In a case where the diffuse reflectance is large, it can be said that the concealing ability is large. Thus, it is preferable that the value is large.

A correlation between the index for concealing ability and an appearance viewed by human's eyes is shown in Table 2.

where the light with which the titanium oxide particles present in the center are irradiated spreads larger (wider) in the display surface. On the other hand, in this simulation, it can be said that a degree of scattering is small in a case

TABLE 1

Evaluation of titanium oxide particles

|  | Average value (nm) of maximum values X, the maximum value being a maximum value of line segments each of which connects two apexes | Proportion (% by number) of octahedral-shaped particles | Specific surface area (m²/g) | BET-converted average particle diameter (nm) | Average value of X/BET-converted average particle diameter | Average value of rations (X/Y) | Evaluation of cosmetics | | |
|---|---|---|---|---|---|---|---|---|---|
|  |  |  |  |  |  |  | Paleness $TR_{450\ nm}/TR_{550\ nm}$ | Feeling of transparency $R_{550\ nm}/TR_{550\ nm}$ | Concealing ability $TR_{550\ nm}$ |
| Example 1 | 350 | 70 | 13 | 312 | 1.1 | 2.0 | 1.02 | 0.01 | 48 |
| Example 2 | 450 | 65 | 9 | 451 | 1.0 | 2.0 | 1.01 | 0.01 | 50 |
| Example 3 | 740 | 60 | 6 | 677 | 1.1 | 2.0 | 1.01 | 0.02 | 53 |
| Comparative Example 1 | 300 | 0 | 6 | 250 | 1.2 | 1.0 | 1.03 | 0.05 | 48 |
| Comparative Example 2 | 300 | 0 | 21 | 100 | 3.0 | 2.2 | 1.13 | 0.02 | 42 |
| Comparative Example 3 | 220 | 70 | 22 | 185 | 1.2 | 2.0 | 1.07 | 0.02 | 42 |
| Comparative Example 4 | 1200 | 65 | 4 | 1015 | 1.2 | 2.0 | 1.01 | 0.04 | 63 |
| Comparative Example 5 | 500 | 0 | 4 | 375 | 1.3 | 1.0 | 1.01 | 0.04 | 58 |

TABLE 2

|  | Numerical value | Appearance viewed by human's eyes |
|---|---|---|
| Paleness $TR_{450\ nm}/TR_{550\ nm}$ | Less than 1.05 | No paleness |
|  | Equal to or greater than 1.05 and less than 1.10 | Slightly pale |
|  | Equal to or greater than 1.10 | Pale |
| Feeling of transparency $R_{550\ nm}/TR_{550\ nm}$ | Less than 0.03 | There is a feeling of transparency |
|  | Equal to or greater than 0.03 and less than 0.05 | There is almost no feeling of transparency |
|  | Equal to or greater than 0.05 | There is no feeling of transparency |
| Concealing ability $TR_{550\ nm}$ | Equal to or greater than 45 | There is a concealing ability |
|  | Equal to or greater than 40 and less than 45 | There is almost no concealing ability |
|  | Less than 40 | There is no concealing ability |

From the above results, it has become clear that due to being capable of achieving both a concealing ability and a feeling of transparency, and having a less pale color tone, the titanium oxide particles of the present invention are suitable for cosmetics for base makeup.

In order to confirm that the octahedral-shaped titanium oxide particles are capable of scattering light over a wide range, the following simulation was performed.

Figure 5:
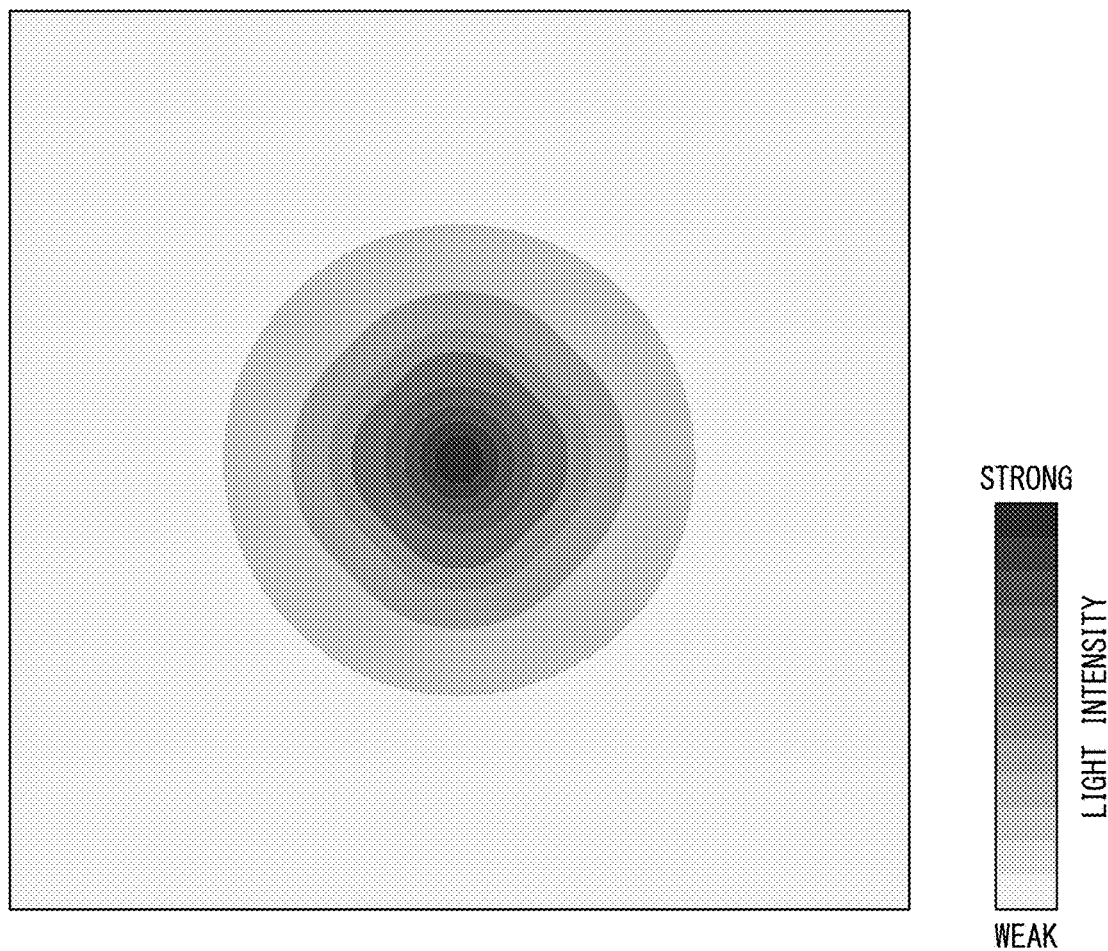
FIG. 5 is a view showing a result of simulating how light scatters in a case where spherical-shaped titanium oxide particles are irradiated with light.
Figure 6:
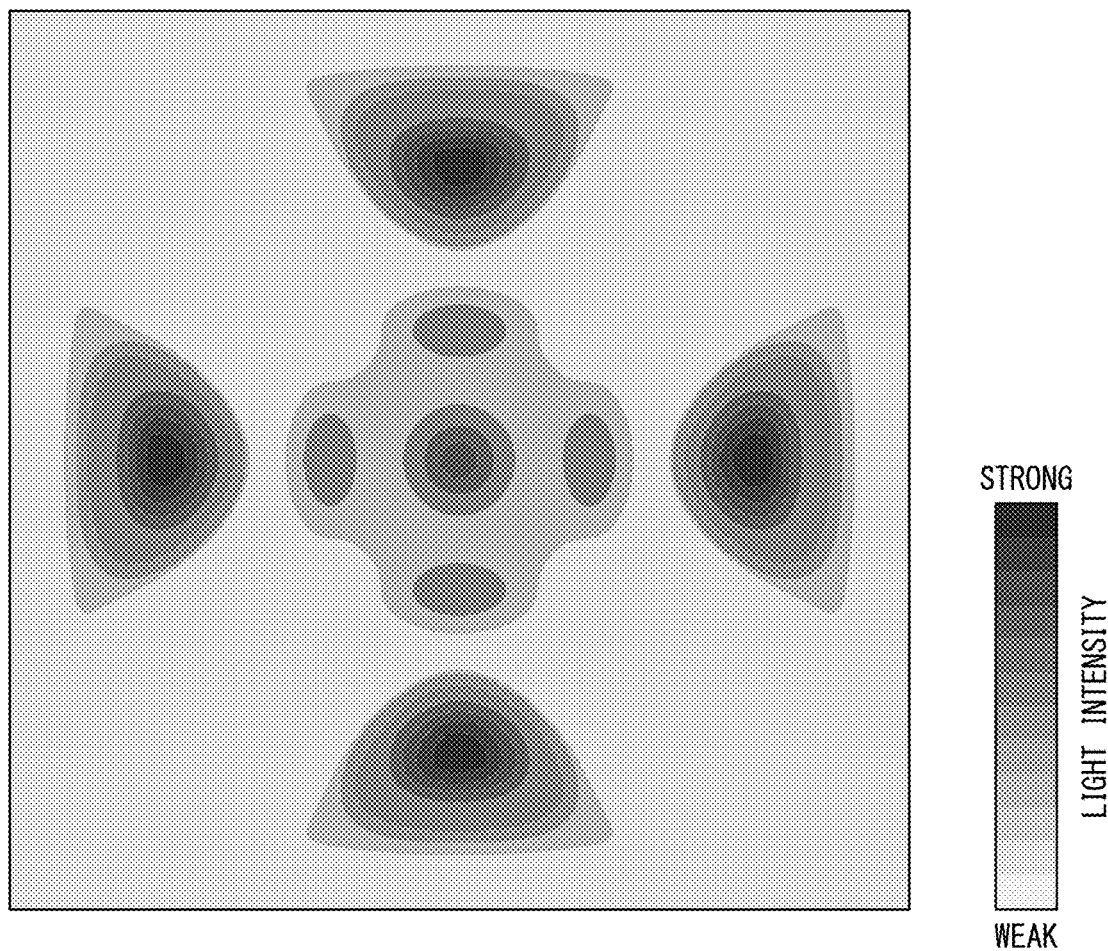
FIG. 6 is a view showing a result of simulating how light scatters in a case where octahedral-shaped titanium oxide particles are irradiated with light.

In a case where spherical-shaped titanium oxide particles having a diameter of 500 nm and octahedral-shaped titanium oxide particles in which a maximum value of distances between two apexes which face each other in each particle is 500 nm are irradiated with light having a wavelength of 700 nm, simulation was performed by the Finite-difference time-domain (FDTD) method on how the light scatters. The simulation results on the spherical-shaped titanium oxide particles are shown in FIG. 5. In addition, the simulation results on the octahedral-shaped titanium oxide particles are shown in FIG. 6. In FIGS. 5 and 6, it is assumed that the titanium oxide particles are present in a center of a square-shaped display surface. Therefore, in this simulation, it can be said that a degree of scattering degree is large in a case where the light with which the titanium oxide particles present in the center are irradiated does not spread or spreads small.

From the results in FIGS. 5 and 6, it was confirmed that the octahedral-shaped titanium oxide particles scatter light up to an about 2 times longer distance than the spherical-shaped titanium oxide particles. Such results show that by making the particles an octahedral shape, it is possible to scatter light over a wide range and to achieve both a concealing ability and a feeling of transparency.

REFERENCE SIGNS LIST

X: Maximum value of line segments each of which connects two apexes which face each other in each particle Y: Minimum value of line segments, each of which is substantially orthogonal to a line segment which corresponds to a maximum value of distances between two apexes which face each other in each particle, and each of which connects two apexes

The invention claimed is:

1. Titanium oxide particles, comprising:
   octahedral-shaped particles,
   wherein the octahedral-shaped particles have line segments each of which connects two apexes which face each other and has a maximum value of the line segments, and an average value of the maximum values is 300 nm or more and 1,000 nm or less,
   wherein a value (the average value of the maximum values/BET-converted average particle diameter) obtained by dividing the average value of the maximum values of the line segments by an average particle diameter converted from a BET specific surface area is 1.0 or more and 2.5 or less.

2. The titanium oxide particles according to claim 1, wherein an amount of the octahedral-shaped particles with respect to an entirety of the particles is 50% by number or more.

3. The titanium oxide particles according to claim 1, wherein a specific surface area of the titanium oxide particles is 5 $m^2/g$ or more and 15 $m^2/g$ or less.

4. The titanium oxide particles according to claim 1, wherein in a case where the maximum value is set as X (nm), and a minimum value of line segments, each of which is substantially orthogonal to a line segment which corresponds to the maximum value, and each of which connects two apexes which face each other in each particle of the octahedral-shaped particles, is set as Y (nm), an average value of ratios (X/Y) of the X to the Y is 1.5 or more and 3.0 or less.

5. The titanium oxide particles according to claim 1, wherein the titanium oxide particles have an inorganic compound or an organic compound on a surface thereof.

6. A titanium oxide particle dispersion, comprising:
   the titanium oxide particles according to claim 1; and
   a dispersion medium.

7. Cosmetics comprising:
   the titanium oxide particles according to claim 1; and
   a cosmetic base.

8. Titanium oxide particles, comprising:
   octahedral-shaped particles, wherein the octahedral-shaped particles have line segments each of which connects two apexes which face each other and has a maximum value of the line segments, and an average value of the maximum values is 300 nm or more and 1,000 nm or less,
   wherein a value (the average value of the maximum values/BET-converted average particle diameter) obtained by dividing the average value of the maximum values of the line segments by an average particle diameter converted from a BET specific surface area is 1.0 or more and 2.5 or less, and
   in a case where the maximum value is set as X (nm), and a minimum value of line segments, each of which is substantially orthogonal to a line segment which corresponds to the maximum value, and each of which connects two apexes which face each other in each particle of the octahedral-shaped particles, is set as Y (nm), an average value of ratios (X/Y) of the X to the Y is 1.5 or more and 3.0 or less.

* * * * *